United States Patent
Abouabdellah et al.

(10) Patent No.: US 7,119,116 B2
(45) Date of Patent: Oct. 10, 2006

(54) DERIVATIVES OF DIOXANE-2-ALKYL CARBAMATES, PREPARATION THEREOF AND APPLICATION THEREOF IN THERAPEUTICS

(75) Inventors: Ahmed Abouabdellah, Thiais (FR); Michele Bas, Pignan (FR); Gihad Dargazanli, Cachan (FR); Christian Hoornaert, Antony (FR); Adrien Tak Li, Fontenay aux Roses (FR); Florence Medaisko, Saint Maur des Fosses (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/062,541

(22) Filed: Feb. 22, 2005

(65) Prior Publication Data

US 2005/0182130 A1    Aug. 18, 2005

Related U.S. Application Data

(63) Continuation of application No. PCT/FR03/02590, filed on Aug. 27, 2003.

(30) Foreign Application Priority Data

Aug. 29, 2002    (FR) .................. 02-10707

(51) Int. Cl.
*A61K 31/36* (2006.01)
*C07D 319/06* (2006.01)
(52) U.S. Cl. ..................... 514/452; 549/373
(58) Field of Classification Search ........ 514/452; 549/373
See application file for complete search history.

(56) References Cited

FOREIGN PATENT DOCUMENTS

EP        0461958      12/1991
WO        WO 97/20836  6/1997

*Primary Examiner*—Taofiq A. Solola
(74) *Attorney, Agent, or Firm*—Balaram Gupta

(57) ABSTRACT

A compound corresponding to general formula (I):

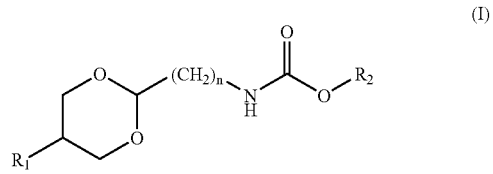

in which $R_1$ represents a phenyl or naphthalenyl group optionally substituted with one or more halogen atoms or hydroxyl, cyano, nitro, $(C_1-C_3)$alkyl, $(C_1-C_3)$alkoxy, trifluoromethyl, trifluoromethoxy, benzyloxy, $(C_3-C_6)$cycloalkyl-O— or $(C_3-C_6)$cycloalkyl$(C_1-C_3)$alkoxy groups; $R_2$ represents either a group of general formula $CHR_3CONHR_4$ in which $R_3$ represents a hydrogen atom or a methyl group and $R_4$ represents a hydrogen atom or a $(C_1-C_3)$alkyl, $(C_3-C_5)$cycloalkyl or (pyridin-4-yl)methyl group; or a 2,2,2-trifluoroethyl group; or an (imidazol-2-yl)methyl group; or a (benzimidazol-2-yl)methyl group; or a phenyl group optionally substituted with one or more halogen atoms or cyano, nitro, $(C_1-C_3)$alkyl, $(C_1-C_3)$alkoxy, trifluoromethyl or trifluoromethoxy groups; and n represents a number ranging from 1 to 3; in the form of a base, of an addition salt with an acid, of a hydrate or of a solvate. Also disclosed and claimed are the pharmaceutical compositions derived therefrom and their therapeutic use in treating a wide variety of diseases.

23 Claims, No Drawings

DERIVATIVES OF DIOXANE-2-ALKYL CARBAMATES, PREPARATION THEREOF AND APPLICATION THEREOF IN THERAPEUTICS

This application is a continuation of International application No. PCT/FR2003/02,590, filed Aug. 27, 2003; which claims the benefit of priority of French Patent Application No. 02/10,707, filed Aug. 29, 2002, both of which are incorporated herein by reference in their entirety.

BACKGROUND OF THE INVENTION

1. Field of the Invention

The invention relates to 1,3-dioxan-2-ylalkylcarbamate derivatives, to their preparation and to their use in therapeutics.

SUMMARY OF THE INVENTION

The compounds of the invention correspond to general formula (I)

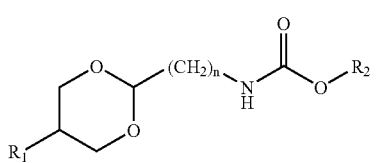

in which
$R_1$ represents a phenyl or naphthalenyl group optionally substituted with one or more halogen atoms or hydroxyl, cyano, nitro, $(C_1–C_3)$alkyl, $(C_1–C_3)$alkoxy, trifluoromethyl, trifluoromethoxy, benzyloxy, $(C_3–C_6)$cycloalkyl-O— or $(C_3–C_6)$cycloalkyl$(C_1–C_3)$alkoxy groups;
$R_2$ represents either a group of general formula $CHR_3CONHR_4$ in which
$R_3$ represents a hydrogen atom or a methyl group and
$R_4$ represents a hydrogen atom or a $(C_1–C_3)$alkyl, $(C_3–C_5)$cycloalkyl or (pyridin-4-yl)methyl group, or a 2,2,2-trifluoroethyl group, or an (imidazol-2-yl)methyl group, or a (benzimidazol-2-yl)methyl group, or a phenyl group optionally substituted with one or more halogen atoms or cyano, nitro, $(C_1–C_3)$alkyl, $(C_1–C_3)$alkoxy, trifluoromethyl or trifluoromethoxy groups; and
n represents a number ranging from 1 to 3.

DETAILED DESCRIPTION OF THE INVENTION

The compounds of general formula (I) may comprise one or more asymmetric carbons. They may exist in the form of enantiomers or of diastereoisomers. The compounds of general formula (I) may also exist in the form of cis or trans stereoisomers. These enantiomers, diastereoisomers and stereoisomers, and also their mixtures, including the racemic mixtures, are part of the invention.

The compounds of formula (I) may exist in the form of bases or of addition salts with acids. Such addition salts are part of the invention.

These salts are advantageously prepared with pharmaceutically acceptable acids, but the salts of other acids which are of use, for example, for purifying or isolating the compounds of formula (I) are also part of the invention. The compounds of general formula (I) may be in the form of hydrates or of solvates, namely in the form of associations or of combinations with one or more molecules of water or with a solvent. Such hydrates and solvates are also part of the invention.

Compounds similar to those of the invention, for which $R_2$ represents a linear or branched $(C_1–C_4)$alkyl group, have been described as anticonvulsants in documents EP 0461958 and FR 2714056; both of which are incorporated herein by reference in their entirety.

In the context of the invention:
the term "$(C_t–C_z)$" where t and z can take the values of 1 to 6" is intended to mean a carbon chain which can have from t to z carbon atoms, for example "$(C_1–C_3)$" is intended to mean a carbon chain which can have from 1 to 3 carbon atoms;
the term "alkyl" is intended to mean a linear or branched, saturated aliphatic group; for example a $(C_1–C_3)$alkyl group represents a linear or branched carbon chain of 1 to 3 carbon atoms, more particularly a methyl, ethyl, propyl or isopropyl;
the term "cycloalkyl" is intended to mean a cyclic alkyl group; for example, a $(C_3–C_5)$cycloalkyl group represents a cyclic carbon chain of 3 to 5 carbon atoms, more particularly a cyclopropyl, cyclobutyl or cyclopentyl;
the term "alkoxy" is intended to mean an alkyloxy group containing a linear or branched, saturated aliphatic chain;
the term "halogen atom" is intended to mean a fluorine, a chlorine, a bromine or an iodine.

Among the compounds of general formula (I), mention may be made of preferred compounds, which are defined as follows:
$R_1$ represents a naphthalenyl group optionally substituted with one or more halogen atoms or hydroxyl, cyano, nitro, $(C_1–C_3)$alkyl, $(C_1–C_3)$alkoxy, trifluoromethyl, trifluoromethoxy, benzyloxy, $(C_3–C_6)$cycloalkyl-O— or $(C_3–C_6)$cycloalkyl$(C_1–C_3)$alkoxy groups; and/or
$R_2$ represents either a group of general formula $CHR_3CONHR_4$ in which
$R_3$ represents a hydrogen atom and
$R_4$ represents a hydrogen atom or a $(C_1–C_3)$alkyl group, preferably a methyl or an ethyl, or (pyridin-4-yl)methyl group, or a 2,2,2-trifluoroethyl group, or a phenyl group optionally substituted with one or more halogen atoms or cyano, nitro, $(C_1–C_3)$alkyl, $(C_1–C_3)$alkoxy, trifluoromethyl or trifluoromethoxy groups; and/or
n represents 2 or 3.

The compounds for which both $R_1$, $R_2$ and n are as defined above are particularly preferred.

By way of example of preferred compounds, mention may be made of the following compounds:
2-amino-2-oxoethyl trans-3-[5-(naphthalen-1-yl)-1,3-dioxan-2-yl]propylcarbamate
2-(methylamino)-2-oxoethyl trans-2-[5-(naphthalen-1-yl)-1,3-dioxan-2-yl]ethylcarbamate
2-(methylamino)-2-oxoethyl trans-3-[5-(naphthalen-1-yl)-1,3-dioxan-2-yl]propylcarbamate
2,2,2-trifluoroethyl trans-2-[5-(naphthalen-1-yl)-1,3-dioxan-2-yl]ethylcarbamate
2,2,2-trifluoroethyl trans-3-[5-(naphthalen-1-yl)-1,3-dioxan-2-yl]propylcarbamate
phenyl trans-2-[5-(naphthalen-1-yl)-1,3-dioxan-2-yl]ethylcarbamate
phenyl trans-3-[5-(naphthalen-1-yl)-1,3-dioxan-2-yl]propylcarbamate
2-amino-2-oxoethyl trans-3-[5-(4-chloronaphthalen-1-yl)-1,3-dioxan-2-yl]propylcarbamate
2-(methylamino)-2-oxoethyl trans-3-[5-(4-chloro-naphthalen-1-yl)-1,3-dioxan-2-yl]propylcarbamate 2-(methylamino)-2-oxoethyl trans-3-[5-(6-chloro-naphthalen-1-yl)-1,3-dioxan-2-yl]propylcarbamate 2-amino-2-oxoethyl trans-3-[5-(6-methoxynaphthalen-1-yl)-1,3-dioxan-2-yl]propylcarbamate 2-amino-2-oxoethyl cis-3-[5-(6-methoxynaphthalen-1-yl)-1,3-dioxan-2-yl]propylcarbamate 2-(methylamino)-2-oxoethyl trans-2-[5-(6-methoxy-naphthalen-1-yl)-1,3-dioxan-2-yl]ethylcarbamate 4-chlorophenyl trans-2-[5-(6-methoxynaphthalen-1-yl)-1,3-dioxan-2-yl]ethylcarbamate 2,2,2-trifluoroethyl trans-2-[5-(6-methoxynaphthalen-1-yl)-1,3-dioxan-2-yl]ethylcarbamate 2-(methylamino)-2-oxoethyl trans-3-[5-(6-methoxy-naphthalen-1-yl)-1,3-dioxan-2-yl]propylcarbamate 2-(ethylamino)-2-oxoethyl trans-3-[5-(6-methoxy-naphthalen-1-yl)-1,3-dioxan-2-yl]propylcarbamate 2-[(pyridin-4-yl)methylamino]-2-oxoethyl trans-3-[5-(6-methoxynaphthalen-1-yl)-1,3-dioxan-2-yl]propylcarbamate 2,2,2-trifluoroethyl trans-3-[5-(6-methoxynaphthalen-1-yl)-1,3-dioxan-2-yl]propylcarbamate phenyl trans-3-[5-(6-methoxynaphthalen-1-yl)-1,3-dioxan-2-yl]propylcarbamate 2-amino-2-oxoethyl trans-3-[5-(6-cyclopropylmethoxy-naphthalen-1-yl)-1,3-dioxan-2-yl]propylcarbamate 4-chlorophenyl trans-3-[5-(6-cyclopropylmethoxy-naphthalen-1-yl)-1,3-dioxan-2-yl]propylcarbamate 2,2,2-trifluoroethyl trans-3-[5-(6-cyclopropylmethoxy-naphthalen-1-yl)-1,3-dioxan-2-yl]propylcarbamate 2-amino-2-oxoethyl trans-3-[5-(6-phenylmethoxy-naphthalen-1-yl)-1,3-dioxan-2-yl]propylcarbamate 2-amino-2-oxoethyl trans-3-[5-(6-hydroxynaphthalen-1-yl)-1,3-dioxan-2-yl]propylcarbamate 2-(methylamino)-2-oxoethyl trans-3-[5-(6-hydroxy-naphthalen-1-yl)-1,3-dioxan-2-yl]propylcarbamate 2-amino-2-oxoethyl trans-3-[5-(7-methoxynaphthalen-1-yl)-1,3-dioxan-2-yl]propylcarbamate 2-(methylamino)-2-oxoethyl trans-3-[5-(7-methoxy-naphthalen-1-yl)-1,3-dioxan-2-yl]propylcarbamate 2,2,2-trifluoroethyl trans-3-[5-(7-methoxynaphthalen-1-yl)-1,3-dioxan-2-yl]propylcarbamate phenyl trans-3-[5-(7-methoxynaphthalen-1-yl)-1,3-dioxan-2-yl]propylcarbamate phenyl trans-3-[5-(naphthalen-2-yl)-1,3-dioxan-2-yl]propylcarbamate 2-(methylamino)-2-oxoethyl trans-3-[5-(naphthalen-2-yl)-1,3-dioxan-2-yl]propylcarbamate 2,2,2-trifluoroethyl trans-3-[5-(naphthalen-2-yl)-1,3-dioxan-2-yl]propylcarbamate.

The compounds of the invention can be prepared according to various methods, illustrated by the following schemes.

Thus, a method of preparation (Scheme 1) consists in reacting an amine of general formula (II), in which $R_1$ and n are as defined in general formula (I), with a carbonate of general formula (III), in which U represents a hydrogen atom or a nitro group and $R_2$ is as defined in general formula (I), in a solvent such as toluene or dichloroethane, at a temperature of between 0 and 80° C.

Scheme 1

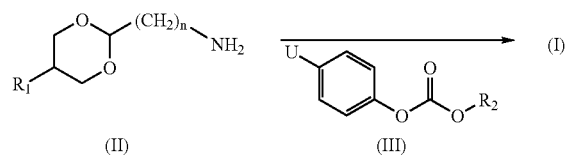

The carbonates of general formula (III) can be prepared according to any method described in the literature, for example by reacting an alcohol of general formula $HOR_2$ with phenyl or 4-nitrophenyl chloroformate, in the presence of a base such as triethylamine or diisopropylethylamine.

The compounds of general formula (I) for which $R_2$ represents more particularly an optionally substituted phenyl group (Ar) can be prepared by reacting an amine of general formula (II), as defined above, with an aryl chloroformate of general formula (IIIa) in a solvent such as dichloromethane or dichloroethane, in the presence of a base such as triethylamine or diisopropylethylamine, at a temperature of between 0° C. and the reflux temperature of the solvent.

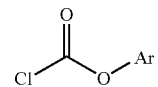

(IIIa)

According to Scheme 2, the compounds of general formula (I) for which $R_2$ represents more particularly a group of general formula $CHR_3CONHR_4$ can be prepared by reacting an amine of general formula (II), as defined above, with carbon dioxide in the presence of a base such as cesium carbonate and a phase-transfer agent such as tetra-n-butylammonium iodide, in a solvent such as N,N-dimethylformamide or N-methylpyrrolidone, and then with a haloacetamide of general formula (IV) in which V represents a chlorine, bromine or iodine atom and $R_3$ and $R_4$ are as defined in general formula (I).

Scheme 2

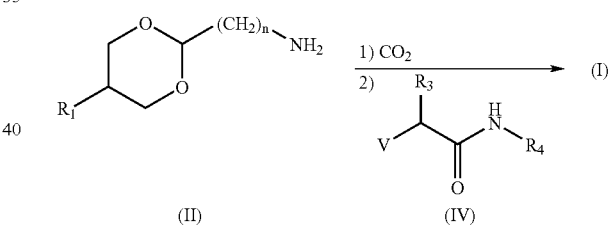

A variant (Scheme 3) for obtaining the compounds of general formula (I) in which $R_2$ represents more particularly a group of general formula $CHR_3CONHR_4$ consists in reacting an amine of general formula (II), as defined above, with a carbonate of general formula (IIIb) in which U represents a hydrogen atom or a nitro group, $R_3$ is as defined in general formula (I) and $R_5$ represents a methyl or ethyl group. The carbamate ester of general formula (Ia) thus obtained is then converted to a compound of general formula (I), either by direct aminolysis by means of an amine of general formula $R_4NH_2$ in which $R_4$ is as defined in general formula (I), or by hydrolysis to an acid of general formula (Ia), in which $R_5$ represents a hydrogen atom, followed by coupling with an amine of general formula $R_4NH_2$ in which $R_4$ is as defined in general formula (I). The aminolysis reaction can be carried out in a solvent such as methanol or a mixture of solvents such as methanol and tetrahydrofuran. The coupling reaction can be carried out according to any known method from the literature, for example using isobutyl chloroformate in the presence of a base such as diisopropylethylamine.

The carbonates of general formula (IIIb) can be prepared in a manner similar to the carbonates of formula (III).

Scheme 3

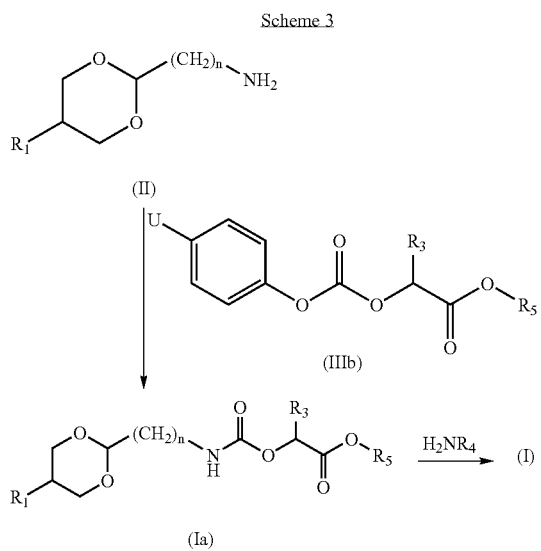

Another variant (Scheme 4) for obtaining the compounds of general formula (I) in which R₂ represents more particularly a group of general formula CHR₃CONHR₄ consists in reacting a derivative of general formula (IIa), in which Z represents a hydroxyl, mesylate or tosylate group, or a chlorine, bromine or iodine atom, and R₁ and n are as defined in general formula (I), with an oxazolidinedione of general structure (V) in which R₃ is as defined in general formula (I), to provide the oxazolidinedione derivative of general structure (VI). When Z represents a hydroxyl group, the reaction can be carried out according to the conditions of Mitsunobu (Synthesis, 1981, 1–28), for example by the action of diethyl or diisopropyl azodicarboxylate in the presence of triphenylphosphine. When Z represents a chlorine, bromine or iodine atom, or a mesylate or tosylate group, the reaction can be carried out in the presence of a base such as 1,1,3,3-tetramethylguanidine, sodium hydride or sodium tert-butoxide in a solvent such as tetrahydrofuran, acetonitrile or dimethylformamide, at a temperature of between 0° C. and the reflux temperature of the solvent. The oxazolidinedione derivative of general formula (VI) thus obtained is then converted to a compound of general formula (I) by aminolysis by means of an amine of general formula R₄NH₂ where R₄ is as defined in general formula (I).

Scheme 4

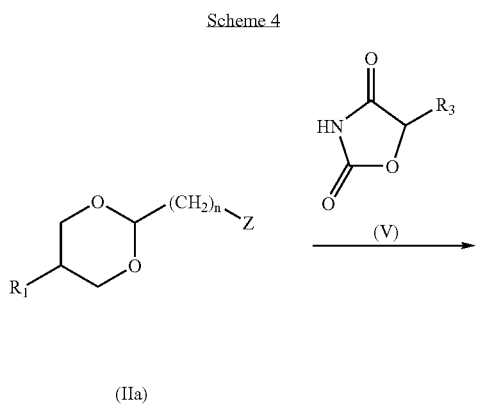

-continued

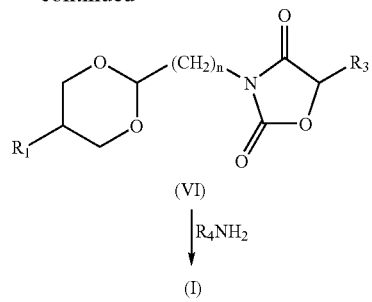

The amines of general formula (II) can be prepared according to the methods of preparation described in patent applications EP 0461958, WO 97/20836 and WO 98/55474, optionally adapted according to techniques known to those skilled in the art. All of the references described herein are incorporated herein by reference in their entirety.

The compounds of general formulae (IIa), (IIIa), (IV) and (V), and also the amines R₄NH₂, when their method of preparation is not described, are commercially available or described in the literature, or else can be prepared according to methods which are described therein or which are known to those skilled in the art.

The compounds of general formula (Ia), in which R₁, R₃ and n are as defined in general formula (I) and R₅ represents a hydrogen atom or a methyl or ethyl group, and the compounds of general formula (VI), in which R₁, R₃ and n are as defined in general formula (I), are novel and are also part of the invention. They are of use as synthetic intermediates for preparing the compounds of general formula (I).

The following examples illustrate the preparation of some compounds of the invention. These examples are not limiting and merely illustrate the invention. The microanalyses, the IR and NMR spectra and/or the LC-MS (liquid chromatography coupled to mass spectroscopy) confirm the structures and the purities of the compounds obtained. The numbers indicated in brackets in the titles of the examples correspond to those of the 1st column of the table hereinafter.

EXAMPLE 1 (COMPOUND NO. 61)

2-(Cyclopropylamino)-2-oxoethyl trans-3-[5-(6-methoxy-naphthalen-1-yl)-1,3-dioxan-2-yl]propyl-carbamate 1.1. Ethyl [(phenoxycarbonyl)oxy]acetate 13.5 ml (105.6 mmol) of phenyl chloroformate are added, dropwise, at ambient temperature to a solution of 10 g (96.15 mmol) of ethyl glycolate and 27 ml (192.3 mmol) of triethylamine in 20 ml of toluene and the mixture is stirred at ambient temperature for 2 h. The salt formed is separated and the filtrate is concentrated under reduced pressure to obtain 20 g of oily product, which are used without modification in the following step.

1.2. Ethyl trans-[[[[3-[5-(6-methoxynaphthalen-1-yl)-1,3-dioxan-2-yl]propyl]amino]carbonyl]oxy]acetate A solution of 10 g (33 mmol) of trans-3-[5-(6-methoxynaphthalen-1-yl)-1,3-dioxan-2-yl]propanamine and 8.9 g (39.8 mmol) of ethyl [(phenoxycarbonyl)oxy]-acetate, obtained in step 1.1, in 500 ml of toluene, is heated at 50° C. for 12 h. The mixture is allowed to return to ambient temperature, the insoluble material is separated by filtration and the filtrate is concentrated under reduced pressure. The residue is taken up with dichloromethane and water, the aqueous phase is separated and extracted three times with dichloromethane, and the pooled organic phases are washed with a saturated aqueous sodium chloride solution and dried over sodium sulfate. After evaporation of the solvent, the residue is purified by chromatography on silica gel, eluting with a 20/80 mixture of ethyl acetate and cyclohexane. Finally, 7 g of pure product are obtained, in the form of an oil which crystallizes:

Melting point: 74–76° C.

1.3. trans-[[[[3-[5-(6-Methoxynaphthalen-1-yl)-1,3-dioxan-2-yl]propyl]amino]carbonyl]oxy]acetic acid 40 ml of a 1N aqueous sodium hydroxide solution are added, dropwise, to a solution of 4 g (9.27 mmol) of ethyl trans-[[[[3-[5-(6-methoxy-naphthalen-1-yl)-1,3-dioxan-2-yl]propyl]amino]-carbonyl]oxy]acetate, obtained in step 1.2, in 40 ml of dimethoxyethane, and the mixture is stirred at ambient temperature for 2 h. The mixture is concentrated under reduced pressure, the residue is dissolved in a minimum of water, 1N hydrochloric acid is added until a pH equal to 4 is obtained, the aqueous phase is extracted three times with dichloromethane, the organic phase is separated and dried over sodium sulfate, and concentration is carried out at reduced pressure to obtain 3 g of acid.

Melting point: 114–116° C.

1.4. 2-(Cyclopropylamino)-2-oxoethyl trans-3-[5-(6-methoxynaphthalen-1-yl)-1,3-dioxan-2-yl]propylcarbamate A solution of 0.169 g (1.24 mmol) of isobutylchloroformate in 5 ml of tetrahydrofuran is added, dropwise, under an inert atmosphere, to a solution of 0.5 g (1.24 mmol) of trans-[[[[3-[5-(6-methoxynaphthalen-1-yl)-1,3-dioxan-2-yl]propyl]amino]-carbonyl]oxy]acetic acid, obtained in step 1.3, and 0.65 ml (3.70 mmol) of N,N-diisopropylethylamine in 10 ml of tetrahydrofuran, cooled to approximately −20° C., while at the same time maintaining the temperature of the reaction medium below −15° C. Stirring is maintained at this temperature for 1 h, then a solution of 0.078 g (1.36 mmol) of cyclopropylamine in 5 ml of tetrahydrofuran is slowly added, and the stirring is continued at −15° C. for 1 h, and then at 20° C. for 10 h. Concentration is carried out under reduced pressure, the residue is taken up with ethyl acetate and water, the organic phase is separated, washed with a saturated aqueous sodium chloride solution and dried over sodium sulfate, concentration is carried out under reduced pressure, and the solid is recrystallized from ethanol. Finally, 0.258 g of pure product is obtained.

Melting point: 176° C.

$^1$H NMR: (CDCl$_3$) δ (ppm) 8.10 (d, 1H); 7.65 (d, 1H); 7.35 (dd, 1H); 7.25 (d, 1H); 7.15 (dd, 1H); 7.05 (d, 1H); 6.20 (broad m, 1H); 5.05 (broad m, 1H); 4.70 (t, 1H); 4.55 (s, 2H); 4.35 (m, 2H); 3.95–3.90 (m, 6H); 3.30 (m, 2H); 2.75 (m, 1H); 1.75 (m, 4H); 0.80 (m, 2H); 0.55 (m, 2H).

EXAMPLE 2 (COMPOUND NO. 49)

2-Amino-2-oxoethyl trans-3-[5-(6-methoxynaphthalen-1-yl)-1,3-dioxan-2-yl]propylcarbamate 20 g (66 mmol) of trans-3-[5-(6-methoxynaphthalen-1-yl)-1,3-dioxan-2-yl]propanamine, 64 g (198 mmol) of cesium carbonate and 73.14 g (198 mmol) of tetra-n-butylammonium iodide in suspension in 400 ml of N,N-dimethylformamide are introduced into a 1 l three-necked round-bottomed flask placed under an inert atmosphere. A stream of carbon dioxide is passed through the suspension, with vigorous stirring, for 2 h. 18.5 g (198 mmol) of chloroacetamide in solution in 70 ml of N,N-dimethylformamide are then added dropwise, and the stream of carbon dioxide is maintained for 5 h, and the stirring is continued at ambient temperature overnight. The salts are separated by filtration, the filtrate is concentrated under reduced pressure, the residue is taken up with ethyl acetate and water, and the organic phase is separated and washed with a 0.1N aqueous hydrochloric acid solution, then a saturated aqueous sodium hydrogen carbonate solution and a saturated aqueous sodium chloride solution. The organic phase is dried over sodium sulfate and the filtrate is concentrated under reduced pressure, the residue is purified by chromatography on silica gel, eluting with a 95/5 mixture of ethyl acetate and methanol, and the solid obtained is recrystallized from ethyl acetate to obtain 6.5 g of pure product.

Melting point: 148–150° C.

$^1$H NMR: (DMSO) δ (ppm) 8.15 (d, 1H); 7.75 (d, 1H); 7.4 (dd, 1H); 7.35 (d, 1H); 7.25 (m, 4H); 7.15 (broad m, 1H); 4.75 (t, 1H); 4.35 (s, 2H); 4.25 (dd, 2H); 3.95 (dd, 2H); 3.90 (s+m, 4H); 3.05 (m, 2H); 1.60 (m, 4H).

EXAMPLE 3 (COMPOUND NO. 3)

2-(Methylamino)-2-oxoethyl trans-2-(5-phenyl-1,3-dioxan-2-yl)ethylcarbamate 3.1. Ethyl trans-[[[[2-(5-phenyl-1,3-dioxan-2-yl)ethyl]amino]carbonyl]oxy]acetate The method of Example 1.2 is used. From 1 g (4.8 mmol) of trans-2-(5-phenyl-1,3-dioxan-2-yl)ethanamine and 1.1 g (4.8 mmol) of ethyl [(phenoxycarbonyl)oxy]acetate, 0.740 g of ester is obtained, in the form of an oil.

3.2. 2-(Methylamino)-2-oxoethyl trans-2-(5-phenyl-1,3-dioxan-2-yl)ethylcarbamate 3.3 ml (6.7 mmol) of a solution of methylamine (2M in tetrahydrofuran) are added, dropwise, to a solution of 0.70 g (2.1 mmol) of ethyl trans-[[[[2-(5-phenyl-1,3-dioxan-2-yl)ethyl]amino]-carbonyl]oxy]acetate, obtained in step 3.1, in 4 ml of methanol, and the mixture is stirred at ambient temperature for 12 h. Concentration is carried out at reduced pressure, and the residue is purified by chromatography on silica gel, eluting with a 90/10 mixture of dichloromethane and methanol. The oil obtained is triturated in diisopropyl ether and 0.450 g of pure product is obtained.

Melting point: 89° C.

$^1$H NMR: (CDCl$_3$) δ (ppm) 7.35–7.20 (m, 3H); 7.15 (dd, 2H); 6.15 (broad m, 1H); 5.45 (broad m, 1H); 4.75 (t, 1H); 4.60 (s, 2H); 4.20 (dd, 2H); 3.80 (dd, 2H); 3.40 (m, 2H); 3.20 (m, 1H); 2.85 (d, 3H); 1.90 (m, 2H)

EXAMPLE 4 (COMPOUND NO. 63)

1H-Imidazol-2-ylmethyl trans-3-[5-(6-methoxynaphthalen-1-yl)-1,3-dioxan-2-yl]propylcarbamate 4.1. Phenyl (1-triphenylmethyl-1H-imidazol-2-yl)methylcarbonate The procedure is carried out as described in Example 1.1. From 3 g (8.80 mmol) of 1-triphenylmethyl-1H-imidazole-2-methanol (*J. Het. Chem.*, (1995), 32, 903–906) and 1.1 ml (8.80 mmol) of phenyl chloroformate, 3.9 g of product are obtained, which is used unmodified in the following step.

4.2. (1-Triphenylmethyl-1H-imidazol-2-yl)methyl trans-3-[5-(6-methoxynaphthalen-1-yl)-1,3-dioxan-2-yl]propylcarbamate The procedure is carried out as described in Example 1.2. From 2.5 g (8.28 mmol) of trans-3-[5-(6-methoxynaphthalen-1-yl)-1,3-dioxan-2-yl]propanamine and 3.8 g (8.28 mmol)of phenyl (1-triphenylmethyl-1H-imidazol-2-yl)methylcarbonate, obtained in step 4.1, 3.2 g of a solid are obtained, in amorphous form.

4.3. 1H-Imidazol-2-ylmethyl trans-3-[5-(6-methoxy-naphthalen-1-yl)-1,3-dioxan-2-yl]propylcarbamate A solution of 0.6 ml (2.83 mmol) of trifluoroacetic acid in 2 ml of dichloromethane is added, dropwise, at ambient temperature, to a solution of 1.9 g (2.83 mmol) of (1-triphenylmethyl-1H-imidazol-2-yl)methyl trans-3-[5-(6-methoxynaphthalen-1-yl)-1,3-dioxan-2-yl]propylcarbamate, obtained in step 4.2, in 150 ml of dichloromethane, and the mixture is stirred at ambient temperature for 12 h. Concentration is carried out under reduced pressure, the residue is taken up with dichloromethane and a saturated aqueous sodium hydrogen carbonate solution, the organic phase is separated, washed with a saturated aqueous sodium chloride solution and dried over sodium sulfate, concentration is carried out under reduced pressure, and the residue is purified by chromatography on silica gel, eluting with a 98/2/0.2 mixture of dichloromethane, methanol and aqueous ammonia. After recrystallization from ethyl acetate, 0.820 g of pure product is finally obtained.

Melting point: 130–132° C.

$^1$H NMR: (CDCl$_3$) δ (ppm) 10.0 (broad m, 1H); 8.10 (d, 1H); 7.65 (d, 1H); 7.35 (dd, 1H); 7.25 (d, 1H); 7.15 (dd, 1H); 7.05 (dd, 1H); 7.00 (s, 2H); 5.15 (m+s, 3H); 4.70 (t, 1H); 4.30 (m, 2H); 3.95–3.90 (m, 6H); 3.30 (m, 2H); 1.85 (m, 4H).

EXAMPLE 5 (COMPOUND NO. 46)

2-Amino-2-oxoethyl trans-3-[5-(4-chloronaphthalen-1-yl)-1,3-dioxan-2-yl]propylcarbamate 5.1. trans-3-[5-(4-Chloronaphthalen-1-yl)-1,3-dioxan-2-yl]-1-propanol 0.75 ml (10 mmol) of 2,3-dihydrofuran and then 0.25 ml of a concentrated aqueous hydrochloric acid solution (37%) are added to a solution of 1.18 g (5 mmol) of 2-(4-chloronaphthalen-1-yl)-1,3-propanediol in 10 ml of dioxane. The mixture is allowed to react overnight at ambient temperature and then 5 ml of water are added. The mixture is stirred for 5 hours and is then diluted in 25 ml of water and 50 ml of dichloromethane. The mixture is separated after settling out and the aqueous phase is extracted with 50 ml of dichloromethane. The organic phases are washed with 25 ml of a saturated aqueous sodium chloride solution, drying is carried out over sodium sulfate and concentration is carried out under reduced pressure. The residue is purified by chromatography on silica gel, eluting with a 70/30 and then 60/40 mixture of cyclohexane and ethyl acetate. After recrystallization from diisopropyl ether, 0.557 g of product is obtained, in the form of white crystals.

Melting point: 127–129° C.

5.2. trans-3-[5-(4-Chloronaphthalen-1-yl)-1,3-dioxan-2-yl] propyl methanesulfonate A solution of 0.256 g (2.23 mmol) of mesyl chloride in 2 ml of dichloromethane is added, dropwise, to a solution of 0.530 g (1.72 mmol) of trans-3-[5-(4-chloronaphthalen-1-yl)-1,3-dioxan-2-yl]-1-propanol prepared in step 5.1 and of 0.48 ml (3.45 mmol) of triethylamine in 8 ml of dichloromethane cooled to 0° C. under an inert atmosphere. The reaction mixture is stirred at 0° C. for 1 hour. 25 ml of water and 50 ml of dichloromethane are added. The mixture is separated off after settling out and the aqueous phase is extracted with 50 ml of dichloromethane. The organic phases are washed with 25 ml of a saturated aqueous sodium chloride solution, drying is carried out over magnesium sulfate and concentration is carried out under vacuum, to obtain 0.66 g of product in the form of a white solid used without modification in the following step.

5.3. trans-3-[3-(5-(4-Chloronaphthalen-1-yl)-1,3-dioxan-2-yl)propyl]-1,3-oxazolidine-2,4-dione A mixture of 0.660 g (1.71 mmol) of trans-3-[5-(4-chloronaphthalen-1-yl)-1,3-dioxan-2-yl]propyl methanesulfonate, obtained in step 5.2, 0.208 g (2.05 mmol) of 1,3-oxazolidine-2,4-dione (J. Med. Chem., 1991, 34, 1542–1543) and 0.396 g (3.43 mmol) of 1,1,3,3-tetramethylguanidine in 10 ml of tetrahydrofuran is refluxed overnight under an inert atmosphere. The residue is taken up in 100 ml of ethyl acetate and 25 ml of water. Separation is carried out after settling out. The organic phase is washed with 25 ml of water and then 25 ml of a saturated aqueous sodium chloride solution. The aqueous phases are re-extracted with 50 ml of ethyl acetate. The organic phases are pooled, dried over sodium sulfate and concentrated under reduced pressure. The residue is purified by chromatography on silica gel, eluting with a 70/30 and then 60/40 mixture of cyclohexane and ethyl acetate, to obtain 0.483 g of product in the form of a white solid.

Melting point:. 125–127° C.

5.4. 2-Amino-2-oxoethyl trans-3-[5-(4-chloronaphthalen-1-yl)-1,3-dioxan-2-yl]propylcarbamate 0.470 g (1.20 mmol) of trans-3-[3-(5-(4-chloronaphthalen-1-yl)-1,3-dioxan-2-yl)propyl]-1,3-oxazolidine-2,4-dione, obtained in step 5.3, is dissolved in 3.5 ml of tetrahydrofuran and 7 ml of a 7N solution of aqueous ammonia in methanol are added. The mixture is allowed to react overnight at ambient temperature and is then evaporated to dryness, and recrystallization is carried out from a mixture of isopropanol and diisopropyl ether, to obtain 0.388 g of product in the form of white crystals.

Melting point: 176–178° C.

LC-MS: M+H=407

$^1$H NMR (DMSO) δ (ppm): 8.35 (d, 1H); 8.25 (d, 1H); 7.8 (m, 3H); 7.4 (d, 1H); 7.25 (m, 2H); 7.15 (s, 1H); 4.75 (t, 1H); 4.3 (s, 2H); 4.2 (m, 2H); 4.0–3.9 (m, 3H); 3.05 (t, 2H); 1.65 (m, 2H); 1.6 (m, 2H).

EXAMPLE 6 (COMPOUND NO. 67)

4-Chlorophenyl trans-3-[5-(6-cyclopropylmethoxynaphthalen-1-yl)-1,3-dioxan-2-yl]propylcarbamate 0.205 g (0.60 mmol) of trans-3-[5-(6-cylcopropylmethoxynaphthalen-1-yl)-1,3-dioxan-2-yl]propylamine is added, in small portions and at ambient temperature, to a solution of 0.110 ml (0.78 mmol) of 4-chlorophenyl chloroformate and 0.205 ml (1.2 mmol) of N,N-diisopropylethylamine in 6 ml of dichloromethane. The mixture is stirred at ambient temperature for 16 hours, then washing is carried out with 5 ml of a saturated sodium bicarbonate solution. The phases are separated and the organic phase is filtered through a hydrophobic sintered glass funnel. The filtrate is concentrated under reduced pressure and the residue is purified by chromatography on silica gel, eluting with an 80/20 mixture of cyclohexane and ethyl acetate. After washing in 5 ml of diisopropyl ether, 0.176 g of a white solid is obtained.

LC-MS: M+H =496

Melting point: 159–162° C.

$^1$H NMR (CDCl$_3$) δ (ppm): 8.10 (d, 1H); 7.65 (d, 1H); 7.45–7.20 (m, 4H); 7.20–7.00 (m, 4H); 5.30 (broad m, 1H); 4.75 (t, 1H); 4.35 (dd, 2H); 4.10–3.80 (m, 5H); 3.50–3.25 (m, 2H); 1.95–1.70 (m, 4H); 1.45–1.20 (m, 1H); 0.80–0.65 (m, 2H); 0.50–0.30 (m, 2H).

EXAMPLE 7 (COMPOUND NO. 68)

2,2,2-Trifluoroethyl trans-3-[5-(6-cyclopropyl-methoxy-naphthalen-1-yl)-1,3-dioxan-2-yl]propyl-carbamate 0.075 ml (1.01 mmol) of 2,2,2-trifluoroethanol is added, dropwise and at ambient temperature, to a suspension of 0.205 g (1.01 mmol) of 4-nitrophenyl chloroformate and 0.555 g (2.02 mmol) N,N-diisopropylaminoethylpolystyrene (Ps-DIEA, 2% DVB, titre=3.66 mmol/g) in 7.1 ml of dichloromethane. The mixture is stirred with orbital shaking and at ambient temperature for 16 hours. The resin is filtered through a cartridge equipped with a sintered glass funnel and rinsing is carried out with 4 ml of dichloromethane. The filtrate is concentrated under reduced pressure and the oily residue thus obtained is taken up in 3.5 ml of 1,2-dichloroethane. 0.134 ml (0.78 mmol) of N,N-diisopropylethylamine and 0.205 g (0.6 mmol) of 3-[5-(6-cyclopropylmethoxynaphthalen-1-yl)-1,3-dioxan-2-yl]propylamine are successively added. This reaction mixture is heated at 60° C. for 16 hours. After cooling, washing is carried out with 20 ml of a 1N sodium hydroxide solution. The phases are separated and the organic phase is filtered through a hydrophobic sintered glass funnel. The filtrate is concentrated under reduced pressure and the residue is purified by chromatography on silica gel, eluting with an 80/20 mixture of cyclohexane and ethyl acetate. After washing in 5 ml of diisopropyl ether, 0.076 g of white solid is obtained.

LC-MS: M+H=468

Melting point: 105–107° C.

$^1$H NMR: (CDCl$_3$) δ (ppm): 8.15 (d, 1H); 7.65 (d, 1H); 7.35 (dd, 1H); 7.25 (m, 1H); 7.15 (d, 1H); 7.10 (d, 1H); 5.15 (broad m, 1H); 4.75 (t, 1H); 4.50 (q, 2H); 4.30 (dd, 2H); 4.10–3.80 (m, 5H); 3.40–3.20 (m, 2H); 1.90–1.65 (m, 4H); 1.45–1.20 (m, 1H); 0.75–0.60 (m, 2H); 0.50–0.35 (2H).

The following table illustrates the chemical structures and the physical properties of some compounds according to the invention. The compounds in the table exhibit the trans relative configuration on the dioxane ring, with the exception of compounds No. 37 and 50, which exhibit the cis relative configuration, and compounds No. 6, 9, 11, 13, 18, 20, 21 and 43, which are in the form of a mixture of the cis and trans stereoisomers. All the compounds in the table are in the form of bases.

TABLE (I)

| No. | R$_1$ | n | R$_2$ | M + H | M.p. (° C.) |
|---|---|---|---|---|---|
| 1. | phenyl | 2 | CH$_2$CONH$_2$ | — | 172–174 |
| 2. | phenyl | 3 | CH$_2$CONH$_2$ | — | 116–118 |
| 3. | phenyl | 2 | CH$_2$CONHCH$_3$ | — | 89 |
| 4. | phenyl | 3 | CH$_2$CONHCH$_3$ | — | 116 |
| 5. | phenyl | 2 | CH$_2$CF$_3$ | 334 | 77–80 |
| 6. | phenyl | 3 | CH$_2$CF$_3$ | 348 | 83–85 |
| 7. | phenyl | 2 | phenyl | 328 | 131–134 |
| 8. | phenyl | 3 | phenyl | 342 | 100–103 |
| 9. | phenyl | 2 | 2-chlorophenyl | 362 | 95–98 |
| 10. | phenyl | 3 | 2-chlorophenyl | 376 | 129–131 |
| 11. | phenyl | 2 | 4-chlorophenyl | 362 | 134–136 |
| 12. | phenyl | 3 | 4-chlorophenyl | 376 | 117–121 |
| 13. | phenyl | 2 | 4-fluorophenyl | 346 | 132–134 |
| 14. | phenyl | 3 | 4-fluorophenyl | 360 | 106–109 |
| 15. | phenyl | 2 | 4-methylphenyl | 342 | 112–115 |
| 16. | phenyl | 3 | 4-methylphenyl | 356 | 87–90 |
| 17. | phenyl | 2 | 2-methoxyphenyl | 358 | — |
| 18. | phenyl | 3 | 2-methoxyphenyl | 372 | 84–87 |
| 19. | phenyl | 2 | 4-methoxyphenyl | 358 | 130–132 |
| 20. | phenyl | 3 | 4-methoxyphenyl | 372 | 99–101 |
| 21. | phenyl | 2 | 3-trifluoromethylphenyl | 396 | 87–90 |
| 22. | phenyl | 3 | 3-trifluoromethylphenyl | 410 | 128–131 |
| 23. | 4-fluorophenyl | 1 | 4-chlorophenyl | — | 139–141 |
| 24. | 4-fluorophenyl | 2 | CH$_2$CONHCH$_3$ | — | 124–126 |
| 25. | 4-fluorophenyl | 3 | CH$_2$CONHCH$_3$ | — | 150–152 |
| 26. | 3-chlorophenyl | 2 | 4-chlorophenyl | — | 123–125 |
| 27. | 3-chlorophenyl | 3 | 4-chlorophenyl | — | 89–91 |
| 28. | 4-chlorophenyl | 1 | 4-chlorophenyl | — | 146–148 |
| 29. | 4-chlorophenyl | 1 | CH$_2$CF$_3$ | — | 99–101 |
| 30. | 2-methoxyphenyl | 2 | 4-chlorophenyl | — | 144–146 |
| 31. | 3-methoxyphenyl | 2 | 4-chlorophenyl | — | 116–118 |
| 32. | 4-methoxyphenyl | 3 | 4-chlorophenyl | — | 128–131 |
| 33. | 3-trifluoromethylphenyl | 1 | 4-chlorophenyl | — | 116–119 |
| 34. | 3-trifluoromethylphenyl | 1 | CH$_2$CF$_3$ | — | 66–67 |
| 35. | 3-trifluoromethylphenyl | 3 | 4-chlorophenyl | — | 93–96 |
| 36. | 3-trifluoromethylphenyl | 2 | CH$_2$CONHCH$_3$ | — | 118–120 |
| 37. | 3-trifluoromethylphenyl | 2 | CH$_2$CONHCH$_3$ | — | 82–84 |
| 38. | naphthalen-1-yl | 3 | CH$_2$CONH$_2$ | — | 112–114 |
| 39. | naphthalen-1-yl | 2 | CH$_2$CONHCH$_3$ | — | 86–88 |
| 40. | naphthalen-1-yl | 3 | CH$_2$CONHCH$_3$ | — | 154 |
| 41. | naphthalen-1-yl | 2 | CH$_2$CF$_3$ | 384 | 111–113 |
| 42. | naphthalen-1-yl | 3 | CH$_2$CF$_3$ | 398 | 89–92 |
| 43. | naphthalen-1-yl | 2 | CH$_2$-benzimidazol-2-yl | 432 | — |
| 44. | naphthalen-1-yl | 2 | phenyl | 378 | 131–133 |
| 45. | naphthalen-1-yl | 3 | phenyl | 392 | 125–127 |
| 46. | 4-chloro-naphthalen-1-yl | 3 | CH$_2$CONH$_2$ | 407 | 176–178 |
| 47. | 4-chloro-naphthalen-1-yl | 3 | CH$_2$CONHCH$_3$ | — | 190–192 |
| 48. | 6-chloro-naphthalen-1-yl | 3 | CH$_2$CONHCH$_3$ | — | 182–184 |
| 49. | 6-methoxy-naphthalen-1-yl | 3 | CH$_2$CONH$_2$ | — | 148–150 |
| 50. | 6-methoxy-naphthalen-1-yl | 3 | CH$_2$CONH$_2$ | — | 144–147 |
| 51. | 6-methoxy-naphthalen-1-yl | 1 | CH$_2$CONHCH$_3$ | — | 194–196 |
| 52. | 6-methoxy-naphthalen-1-yl | 1 | 4-chlorophenyl | — | 133–136 |
| 53. | 6-methoxy-naphthalen-1-yl | 1 | CH$_2$CF$_3$ | — | 142–144 |
| 54. | 6-methoxy-naphthalen-1-yl | 2 | CH$_2$CONHCH$_3$ | — | 136–138 |
| 55. | 6-methoxy-naphthalen-1-yl | 2 | 4-chlorophenyl | — | 129–131 |
| 56. | 6-methoxy-naphthalen-1-yl | 2 | CH$_2$CF$_3$ | — | 93–95 |

TABLE-continued $$\text{(I)}$$

Structure: R₁-substituted 1,3-dioxane with -(CH₂)ₙ-NH-C(=O)-O-R₂

| No. | R₁ | n | R₂ | M + H | M.p. (° C.) |
|---|---|---|---|---|---|
| 57. | 6-methoxy-naphthalen-1-yl | 3 | CH₂CONHCH₃ | — | 128–130 |
| 58. | 6-methoxy-naphthalen-1-yl | 3 | CH₂CONHCH₂CH₃ | — | 170–172 |
| 59. | 6-methoxy-naphthalen-1-yl | 3 | CH(CH₃)CONHCH₃ | — | 154 |
| 60. | 6-methoxy-naphthalen-1-yl | 3 | CH₂CONHCH₂-pyridin-4-yl | — | 152 |
| 61. | 6-methoxy-naphthalen-1-yl | 3 | CH₂CONH-cyclopropyl | — | 176 |
| 62. | 6-methoxy-naphthalen-1-yl | 3 | CH₂CF₃ | — | 111 |
| 63. | 6-methoxy-naphthalen-1-yl | 3 | CH₂-imidazol-2-yl | — | 130–132 |
| 64. | 6-methoxy-naphthalen-1-yl | 3 | CH₂-benzimidazol-2-yl | — | 175–176 |
| 65. | 6-methoxy-naphthalen-1-yl | 3 | phenyl | — | 128 |
| 66. | 6-cyclopropyl-methoxy-naphthalen-1-yl | 3 | CH₂CONH₂ | — | 137–139 |
| 67. | 6-cyclopropyl-methoxy-naphthalen-1-yl | 3 | 4-chlorophenyl | 496 | 159–162 |
| 68. | 6-cyclopropyl-methoxy-naphthalen-1-yl | 3 | CH₂CF₃ | 468 | 105–107 |
| 69. | 6-phenyl-methoxy-naphthalen-1-yl | 1 | CH₂CONH₂ | — | 154–156 |
| 70. | 6-hydroxy-naphthalen-1-yl | 3 | CH₂CONH₂ | — | 166–170 |
| 71. | 6-hydroxy-naphthalen-1-yl | 3 | CH₂CONHCH₃ | — | 140–148 |
| 72. | 7-methoxy-naphthalen-1-yl | 3 | CH₂CONH₂ | — | 156–158 |
| 73. | 7-methoxy-naphthalen-1-yl | 3 | CH₂CONHCH₃ | — | 144–146 |
| 74. | 7-methoxy-naphthalen-1-yl | 3 | CH₂CF₃ | 428 | 93–96 |
| 75. | 7-methoxy-naphthalen-1-yl | 3 | phenyl | 422 | 151–153 |
| 76. | naphthalen-2-yl | 3 | phenyl | 392 | 130–131 |
| 77. | naphthalen-2-yl | 3 | CH₂CONHCH₃ | — | 144–146 |
| 78. | naphthalen-2-yl | 3 | CH₂CF₃ | 398 | 130–132 |

The compounds of the invention have been the subject of pharmacological tests to determine their inhibitory effect on the enzyme FAAH (Fatty Acid Amido Hydrolase).

The inhibitory activity was demonstrated in a radioenzymatic assay based on measuring the product of hydrolysis (ethanolamine [1-$^3$H]) of anandamide [ethanolamine 1-$^3$H] by FAAH (*Life Sciences* (1995), 56, 1999–2005 and *Journal of Pharmacology and Experimented Therapeutics* (1997), 283, 729–734). Thus, mouse brains (minus the cerebellum) are removed and stored at −80° C. Membrane homogenates are prepared extemporaneously by homogenization of the tissues with a Polytron in a 10 mM Tris-HCl buffer (pH 8.0) containing 150 mM NaCl and 1 mM EDTA. The enzyme reaction is then carried out in 70 µl of buffer containing bovine serum albumin without fatty acids (1 mg/ml). The compounds tested, at various concentrations, the anandamide [ethanolamine 1-$^3$H] (specific activity of 15–20 Ci/mmol) diluted to 10 µM with non-radiolabeled anandamide and the membrane preparation (400 µg of frozen tissue per assay) are added successively. After 15 minutes at 25° C., the enzyme reaction is stopped by adding 140 µl of chloroform/methanol (2:1). The mixture is stirred for 10 minutes and then centrifuged for 15 minutes at 3 500 g. An aliquot (30 µl) of the aqueous phase containing the ethanolamine [1-$^3$H] is counted by liquid scintillation.

Under these conditions, the most active compounds of the invention exhibit IC$_{50}$ values (concentration which inhibits by 50% the control enzyme activity of FAAH) of between 0.005 and 1 µM.

It therefore appears that the compounds according to the invention have an inhibitory activity on the FAAH enzyme.

The in vivo activity of the compounds of the invention was evaluated in a test for analgesia. Thus, intraperitoneal (i.p.) administration of PBQ (phenylbenzoquinone, 2 mg/kg in a solution of 0.9% NaCl containing 5% of ethanol) to male OF1 mice weighing 25 to 30 g causes abdominal pulls, on average 30 twists or contractions during the 5 to 15 minute period after injection. The compounds tested are administered orally or i.p. in suspension in Tween 80 at 0.5%, 30 minutes, 60 minutes or 120 minutes before administration of PBQ. Under these conditions, the most potent compounds of the invention reduce by 50 to 70% the number of pulls induced by the PBQ, within a dose range of between 1 and 30 mg/kg.

The FAAH enzyme (*Chemistry and Physics of Lipids*, (2000), 108, 107–121) catalyzes the hydrolysis of endogenous derivatives of amides and of esters of various fatty acids such as N-arachidonoylethanolamine (anandamide), N-palmitoylethanolamine, N-oleoylethanolamine, oleamide or 2-arachidonoylglycerol. These derivatives exercise various pharmacological activities by interacting, inter alia, with cannabinoid and vanilloid receptors. The compounds of the invention block this degradation pathway and increase the tissue level of these endogenous substances. They can be used in this respect in the prevention and treatment of any pathological condition in which endogenous cannabinoids and/or any other substrate metabolized by the FAAH enzyme are involved.

The following diseases and conditions may, for example, be mentioned:

pain, in particular acute or chronic pain of the neurogenic type: migraine, neuropathic pain including forms associated with the herpes virus and with diabetes;

acute or chronic pain associated with inflammatory diseases: arthritis, rheumatoid arthritis, osteoarthritis, spondylitis, gout, vasculitis, Crohn's disease, irritable bowel syndrome;

acute or chronic peripheral pain;

dizziness, vomiting, nausea, in particular subsequent to chemotherapy;

eating disorders, in particular anorexia and cachexia of various natures;

neurological and psychiatric pathological conditions: shaking, dyskinesia, dystonia, spasticity, obsessive-compulsive behavior, Tourette's syndrome, all forms of depression and of anxiety of any nature and cause, mood disorders, psychoses;

acute or chronic neurodegenerative diseases: Parkinson's disease, Alzheimer's disease, senile dementia, Huntington's chorea, lesions associated with cerebral ischemia and with cranial and medullary trauma;

epilepsy;

sleep disorders including sleep apnea;

cardiovascular diseases, in particular hypertension, cardiac arrhythmias, arteriosclerosis, heart attack, cardiac ischemias;

renal ischemia;

cancers: benign skin tumors, papillomas and brain tumors, prostate tumors, brain tumors (glioblastomas, medulloepitheliomas, medulloblastomas, neuroblastomas, tumors of embryonic origin, astrocytomas, astroblastomas, ependyomas, oligodendroglyomas, plexus tumor, neuroepitheliomas, epiphyseal tumor, ependymoblastomas, malignant meningiomas, sarcomatosis, malignant melanomas, schwannomas);

disorders of the immune system, in particular autoimmune diseases: psoriasis, lupus erythematosus, diseases of the connective tissue or collagen diseases, Sjögren's syndrome, ankylosing spondylarthritis, undifferentiated spondylarthritis, Behcet's disease, haemolytic autoimmune anaemias, multiple sclerosis, amyotrophic lateral sclerosis, amyloses, transplant rejection, diseases affecting the plasmocytic line; allergic diseases: immediate or delayed hypersensitivity, allergic rhinitis or conjunctivitis, contact dermatitis;

parasitic, viral or bacterial infectious diseases: AIDS: meningitis inflammatory diseases, in particular diseases of the joints: arthritis, rheumatoid arthritis, osteoarthritis, spondylitis, gout, vasculitis, Crohn's disease, irritable bowel syndrome;

osteoporosis;

ocular conditions: ocular hypertension, glaucoma; pulmonary conditions: diseases of the respiratory tracts, bronchospasms, coughing, asthma, chronic bronchitis, chronic obstruction of the respiratory tracts, emphysema;

gastrointestinal diseases: irritable bowel syndrome, intestinal inflammatory disorders, ulcers, diarrhea, gastroesophageal reflux;

urinary incontinence and bladder inflammation.

The use of the compounds according to the invention, for preparing a medicinal product intended to prevent or treat the abovementioned pathological conditions, is an integral part of the invention.

A subject of the invention is also medicinal products which comprise a compound of formula (I), or a salt, or else a hydrate or a solvate, which is pharmaceutically acceptable, of the compound of formula (I). These medicinal products find their use in therapeutics, in particular in the prevention and treatment of the abovementioned pathological conditions.

According to another of its aspects, the present invention concerns pharmaceutical compositions containing, as active principle, at least one compound according to the invention. These pharmaceutical compositions contain an effective dose of a compound according to the invention, or a salt, or a hydrate, or a solvate, which is pharmaceutically acceptable, of said compound and, optionally, one or more pharmaceutically acceptable excipients.

Said excipients are chosen, depending on the pharmaceutical form and the method of administration desired, from the usual excipients which are known to those skilled in the art.

In the pharmaceutical compositions of the present invention for oral, sublingual, subcutaneous, intramuscular, intravenous, topical, local, intrathecal, intranasal, transdermal, pulmonary, ocular or rectal administration, the active principle of formula (I) above, or its optional salt, solvate or hydrate, can be administered in a single-dose administration form, as a mixture with conventional pharmaceutical excipients, to animals and to humans, for preventing or treating the abovementioned disorders or diseases.

Suitable single-dose administration forms comprise oral forms such as tablets, soft or hard gelatin capsules, powders, granules, chewing gums and oral solutions or suspensions, forms for sublingual, buccal, intratracheal, intraocular and intranasal administration and for administration by inhalation, forms for subcutaneous, intramuscular, intravenous or intrathecal administration and forms for rectal or vaginal administration. For topical application, the compounds according to the invention can be used in creams, ointments or lotions.

By way of example, a single-dose administration form for a compound according to the invention in tablet form can comprise the following components:

| | |
|---|---|
| compound according to the invention | 50.0 mg |
| mannitol | 223.75 mg |
| sodium croscaramellose | 6.0 mg |
| corn starch | 15.0 mg |
| hydroxypropylmethylcellulose | 2.25 mg |
| magnesium stearate | 3.0 mg |

Said single-dose forms contain a dose so as to allow daily administration of 0.01 to 20 mg of active principle per kg of body weight, depending on the pharmaceutical form.

There may be particular cases in which higher or lower doses are suitable; such doses also belong to the invention. According to usual practice, the appropriate dose for each patient is determined by the physician, depending on the method of administration, and the weight and response of said patient.

According to another of its aspects, the invention also concerns a method for treating the pathological conditions indicated above, which comprises administering an effective dose of a compound according to the invention, of one of its pharmaceutically acceptable salts, or of a solvate or of a hydrate of said compound.

What is claimed is:

1. A compound corresponding to formula (I)

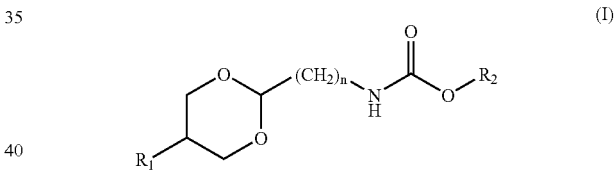

in which $R_1$ represents a phenyl or naphthalenyl group optionally substituted with one or more halogen atoms or hydroxyl, cyano, nitro, $(C_1-C_3)$alkyl, $(C_1-C_3)$alkoxy, trifluoromethyl, trifluoromethoxy, benzyloxy, $(C_3-C_6)$ cycloalkyl-O— or $(C_3-C_6)$cycloalkyl$(C_1-C_3)$alkoxy groups;

$R_2$ represents either a group of general formula $CHR_3CONHR_4$, or a 2,2,2-trifluoroethyl group, or an (imidazol-2-yl)methyl group, or a (benzimidazol-2-yl) methyl group, or a phenyl group optionally substituted with one or more halogen atoms or cyano, nitro, $(C_1-C_3)$alkyl, $(C_1-C_3)$alkoxy, trifluoromethyl or trifluoromethoxy groups; and wherein $R_3$ represents a hydrogen atom or a methyl group;

$R_4$ represents a hydrogen atom or a $(C_1-C_3)$alkyl, $(C_3-C_5)$cycloalkyl or (pyridin-4-yl)methyl group;

n represents a number ranging from 1 to 3; and said compound in the form of a base, an addition salt with an acid.

2. The compound of formula (I) as set forth in claim 1, wherein $R_1$ represents a naphthalenyl group optionally substituted with one or more halogen atoms or hydroxyl, cyano, nitro, $(C_1-C_3)$alkyl, $(C_1-C_3)$alkoxy, trifluoromethyl, trifluoromethoxy, benzyloxy, $(C_3–C_6)$cycloalkyl-O— or $(C_3–C_6)$-cycloalkyl$(C_1–C_3)$alkoxy groups, and said compound in the form of a base or an addition salt with an acid.

3. The compound of formula (I) as set forth in claim 1, wherein $R_2$ represents either a group of general formula $CHR_3CONHR_4$, or a 2,2,2-trifluoroethyl group, or a phenyl group optionally substituted with one or more halogen atoms or cyano, nitro, $(C_1–C_3)$alkyl, $(C_1–C_3)$alkoxy, trifluoromethyl or trifluoromethoxy groups; and
wherein
$R_3$ represents a hydrogen atom;
$R_4$ represents a hydrogen atom or a $(C_1–C_3)$alkyl or (pyridin-4-yl)methyl group; and
said compound in the form of a base or an addition salt with an acid.

4. The compound of formula (I) as set forth in claim 1, wherein n represents 2 or 3;
and said compound is in the form of a base, an addition salt with an acid.

5. The compound of formula (I) as set forth in claim 1, which is chosen from:
2-amino-2-oxoethyl trans-3-[5-(naphthalen-1-yl)-1,3-dioxan-2-yl]propylcarbamate;
2-(methylamino)-2-oxoethyl trans-2-[5-(naphthalen-1-yl)-1,3-dioxan-2-yl]ethylcarbamate;
2-(methylamino)-2-oxoethyl trans-3-[5-(naphthalen-1-yl)-1,3-dioxan-2-yl]propylcarbamate;
2,2,2-trifluoroethyl trans-2-[5-(naphthalen-1-yl)-1,3-dioxan-2-yl]ethylcarbamate;
2,2,2-trifluoroethyl trans-3-[5-(naphthalen-1-yl)-1,3-dioxan-2-yl]propylcarbamate;
phenyl trans-2-[5-(naphthalen-1-yl)-1,3-dioxan-2-yl]ethylcarbamate;
phenyl trans-3-[5-(naphthalen-1-yl)-1,3-dioxan-2-yl]propylcarbamate;
2-amino-2-oxoethyl trans-3-[5-(4-chloronaphthalen-1-yl)-1,3-dioxan-2-yl]propylcarbamate;
2-(methylamino)-2-oxoethyl trans-3-[5-(4-chloronaphthalen-1-yl)-1,3-dioxan-2-yl]propylcarbamate;
2-(methylamino)-2-oxoethyl trans-3-[5-(6-chloronaphthalen-1-yl)-1,3-dioxan-2-yl]propylcarbamate;
2-amino-2-oxoethyl trans-3-[5-(6-methoxynaphthalen-1-yl)-1,3-dioxan-2-yl]propylcarbamate;
2-amino-2-oxoethyl cis-3-[5-(6-methoxynaphthalen-1-yl)-1,3-dioxan-2-yl]propylcarbamate;
2-(methylamino)-2-oxoethyl trans-2-[5-(6-methoxynaphthalen-1-yl)-1,3-dioxan-2-yl]ethylcarbamate;
4-chlorophenyl trans-2-[5-(6-methoxynaphthalen-1-yl)-1,3-dioxan-2-yl]ethylcarbamate;
2,2,2-trifluoroethyl trans-2-[5-(6-methoxynaphthalen-1-yl)-1,3-dioxan-2-yl]ethylcarbamate;
2-(methylamino)-2-oxoethyl trans-3-[5-(6-methoxynaphthalen-1-yl)-1,3-dioxan-2-yl]propylcarbamate;
2-(ethylamino)-2-oxoethyl trans-3-[5-(6-methoxynaphthalen-1-yl)-1,3-dioxan-2-yl]propylcarbamate;
2-[(pyridin-4-yl)methylamino]-2-oxoethyl trans-3-[5-(6-methoxynaphthalen-1-yl)-1,3-dioxan-2-yl]propylcarbamate;
2,2,2-trifluoroethyl trans-3-[5-(6-methoxynaphthalen-1-yl)-1,3-dioxan-2-yl]propylcarbamate;
phenyl trans-3-[5-(6-methoxynaphthalen-1-yl)-1,3-dioxan-2-yl]propylcarbamate;
2-amino-2-oxoethyl trans-3-[5-(6-cyclopropylmethoxynaphthalen-1-yl)-1,3-dioxan-2-yl]propylcarbamate;
4-chlorophenyl trans-3-[5-(6-cyclopropylmethoxynaphthalen-1-yl)-1,3-dioxan-2-yl]propylcarbamate;
2,2,2-trifluoroethyl trans-3-[5-(6-cyclopropylmethoxynaphthalen-1-yl)-1,3-dioxan-2-yl]propylcarbamate;
2-amino-2-oxoethyl trans-3-[5-(6-phenylmethoxynaphthalen-1-yl)-1,3-dioxan-2-yl]propylcarbamate;
2-amino-2-oxoethyl trans-3-[5-(6-hydroxynaphthalen-1-yl)-1,3-dioxan-2-yl]propylcarbamate;
2-(methylamino)-2-oxoethyl trans-3-[5-(6-hydroxynaphthalen-1-yl)-1,3-dioxan-2-yl]propylcarbamate;
2-amino-2-oxoethyl trans-3-[5-(7-methoxynaphthalen-1-yl)-1,3-dioxan-2-yl]propylcarbamate;
2-(methylamino)-2-oxoethyl trans-3-[5-(7-methoxynaphthalen-1-yl)-1,3-dioxan-2-yl]propylcarbamate;
2,2,2-trifluoroethyl trans-3-[5-(7-methoxynaphthalen-1-yl)-1,3-dioxan-2-yl]propylcarbamate;
phenyl trans-3-[5-(7-methoxynaphthalen-1-yl)-1,3-dioxan-2-yl]propylcarbamate;
phenyl trans-3-[5-(naphthalen-2-yl)-1,3-dioxan-2-yl]propylcarbamate;
2-(methylamino)-2-oxoethyl trans-3-[5-(naphthalen-2-yl)-1,3-dioxan-2-yl]propylcarbamate; and
2,2,2-trifluoroethyl trans-3-[5-(naphthalen-2-yl)-1,3-dioxan-2-yl]propylcarbamate; or
said compound in the form of a base or an addition salt with an acid.

6. A method for preparing a compound of formula (I),

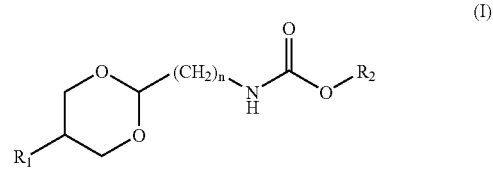

(I)

in which
$R_1$ represents a phenyl or naphthalenyl group optionally substituted with one or more halogen atoms or hydroxyl, cyano, nitro, $(C_1–C_3)$alkyl, trifluoromethyl, trifluoromethoxy, benzyloxy, $(C_3–C_6)$cycloalkyl-O— or $(C_3–C_6)$cycloalkyl$(C_1–C_3)$alkoxy groups;
$R_2$ represents a group of general formula $CHR_3CONHR_4$ or a $(C_1–C_3)$alkyl, $(C_3–C_5)$cycloalkyl or (pyridin-4-yl)methyl group; and
wherein
$R_3$ represents a hydrogen atom or a methyl group;
$R_4$ represents a hydrogen atom or a $(C_1–C_3)$alkyl, $(C_3–C_5)$cycloalkyl or (pyridin-4-yl)methyl group;
n represents a number ranging from 1 to 3;
comprising the step consisting in converting the carbamate ester of general formula (Ia)

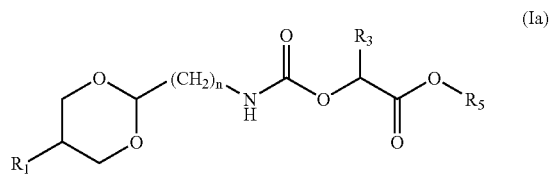

(Ia)

in which $R_1$, $R_3$ and n are as defined above and $R_5$ represents a methyl or ethyl group, to a compound of general formula (I), either by direct aminolysis by means of an amine of general formula $R_4NH_2$ in which $R_4$ is as defined above, or by hydrolysis to an acid of general formula (Ia), in which $R_5$ represents a hydrogen 7. A method for preparing a compound of formula (I),

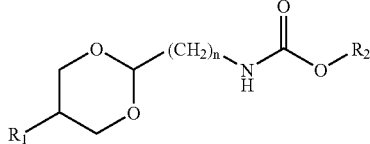

in which

R$_1$ represents a phenyl or naphthalenyl group optionally substituted with one or more halogen atoms or hydroxyl, cyano, nitro, (C$_1$–C$_3$)alkyl, (C$_1$–C$_3$)alkoxy, trifluoromethyl, trifluoromethoxy, benzyloxy, (C$_3$–C$_6$)cycloalkyl-O— or (C$_3$–C$_6$)cycloalkyl(C$_1$–C$_3$)alkoxy groups;

R$_2$ represents a group of general formula CHR$_3$CONHR$_4$ in which R$_3$ represents a hydrogen atom or a methyl group and R$_4$ represents a hydrogen atom or a (C$_1$–C$_3$) alkyl, (C$_3$–C$_5$)cycloalkyl or (pyridin-4-yl)methyl group; and n represents a number ranging from 1 to 3;

comprising the step consisting in converting the oxazolidinedione derivative of general formula (VI)

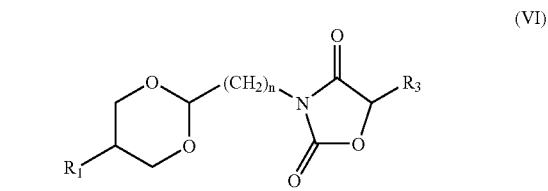

in which R$_1$, R$_3$ and n are as defined above, to a compound of general formula (I) by aminolysis by means of an amine of general formula R$_4$NH$_2$ where R$_4$ is as defined above.

8. A compound corresponding to general formula (Ia)

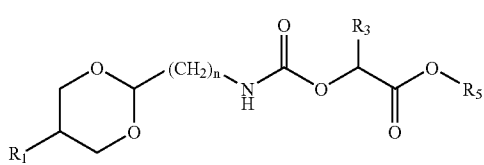

in which

R$_1$ represents a phenyl or a naphthalenyl group optionally substituted with one or more halogen atoms or hydroxyl, cyano, nitro, (C$_1$–C$_3$)alkyl, (C$_1$–C$_3$)alkoxy, trifluoromethyl, trifluoromethoxy, benzyloxy or (C$_3$–C$_6$)cycloalkyl(C$_1$–C$_3$)alkoxy groups;

R$_3$ represents a hydrogen atom or a methyl group;

R$_5$ represents a hydrogen atom, or a methyl or ethyl group; and n represents a number ranging from 1 to 3.

9. A compound corresponding to general formula (VI)

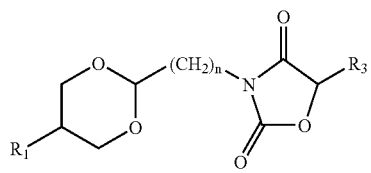

in which

R$_1$ represents a phenyl or naphthalenyl group optionally substituted with one or more halogen atoms or hydroxyl, cyano, nitro, (C$_1$–C$_3$)alkyl, (C$_1$–C$_3$)alkoxy, trifluoromethyl, trifluoromethoxy, benzyloxy or (C$_3$–C$_6$)cycloalkyl(C$_1$–C$_3$)alkoxy groups;

R$_3$ represents a hydrogen atom or a methyl group; and n represents a number ranging from 1 to 3.

10. A pharmaceutical composition comprising at least one compound of formula (I) as set forth in claim 1, in the form of a pharmaceutically acceptable base or salt, in combination with one or more pharmaceutically acceptable excipients.

11. The composition as set forth in claim 10, wherein compound of formula I in which R$_1$ represents a naphthalenyl group optionally substituted with one or more halogen atoms or hydroxyl, cyano, nitro, (C$_1$–C$_3$)alkyl, (C$_1$–C$_3$) alkoxy, trifluoromethyl, trifluoromethoxy, benzyloxy, (C$_3$–C$_6$)cycloalkyl-O— or (C$_3$–C$_6$)-cycloalkyl(C$_1$–C$_3$) alkoxy groups, and said compound in the form of a base or an addition salt with an acid.

12. The composition as set forth in claim 10, wherein compound of formula I in which R$_2$ represents either a group of general formula CHR$_3$CONHR$_4$, or a 2,2,2-trifluoroethyl group, or a phenyl group optionally substituted with one or more halogen atoms or cyano, nitro, (C$_1$–C$_3$)alkyl, (C$_1$–C$_3$) alkoxy, trifluoromethyl or trifluoromethoxy groups; and wherein R$_3$ represents a hydrogen atom and R$_4$ represents a hydrogen atom or a (C$_1$–C$_3$)alkyl or (pyridin-4-yl)methyl group; and said compound in the form of a base an addition salt with an acid.

13. The composition as set forth in claim 10, wherein compound of formula I in which n represents 2 or 3; and said compound is in the form of a base or an addition salt with an acid.

14. The composition as set forth in claim 10, wherein compound of formula I is selected from the group consisting of:

2-amino-2-oxoethyl trans-3-[5-(naphthalen-1-yl)-1,3-dioxan-2-yl]propylcarbamate;

2-(methylamino)-2-oxoethyl trans-2-[5-(naphthalen-1-yl)-1,3-dioxan-2-yl]ethylcarbamate;

2-(methylamino)-2-oxoethyl trans-3-[5-(naphthalen-1-yl)-1,3-dioxan-2-yl]propylcarbamate;

2,2,2-trifluoroethyl trans-2-[5-(naphthalen-1-yl)-1,3-dioxan-2-yl]ethylcarbamate;

2,2,2-trifluoroethyl trans-3-[5-(naphthalen-1-yl)-1,3-dioxan-2-yl]propylcarbamate;

phenyl trans-2-[5-(naphthalen-1-yl)-1,3-dioxan-2-yl]ethylcarbamate;

phenyl trans-3-[5-(naphthalen-1-yl)-1,3-dioxan-2-yl]propylcarbamate;

2-amino-2-oxoethyl trans-3-[5-(4-chloronaphthalen-1-yl)-1,3-dioxan-2-yl]propylcarbamate;

2-(methylamino)-2-oxoethyl trans-3-[5-(4-chloronaphthalen-1-yl)-1,3-dioxan-2-yl]propylcarbamate;
2-(methylamino)-2-oxoethyl trans-3-[5-(6-chloronaphthalen-1-yl)-1,3-dioxan-2-yl]propylcarbamate;
2-amino-2-oxoethyl trans-3-[5-(6-methoxynaphthalen-1-yl)-1,3-dioxan-2-yl]propylcarbamate;
2-amino-2-oxoethyl cis-3-[5-(6-methoxynaphthalen-1-yl)-1,3-dioxan-2-yl]propylcarbamate;
2-(methylamino)-2-oxoethyl trans-2-[5-(6-methoxynaphthalen-1-yl)-1,3-dioxan-2-yl]ethylcarbamate;
4-chlorophenyl trans-2-[5-(6-methoxynaphthalen-1-yl)-1,3-dioxan-2-yl]ethylcarbamate;
2,2,2-trifluoroethyl trans-2-[5-(6-methoxynaphthalen-1-yl)-1,3-dioxan-2-yl]ethylcarbamate;
2-(methylamino)-2-oxoethyl trans-3-[5-(6-methoxynaphthalen-1-yl)-1,3-dioxan-2-yl]propylcarbamate;
2-(ethylamino)-2-oxoethyl trans-3-[5-(6-methoxynaphthalen-1-yl)-1,3-dioxan-2-yl]propylcarbamate;
2-[(pyridin-4-yl)methylamino]-2-oxoethyl trans-3-[5-(6-methoxynaphthalen-1-yl)-1,3-dioxan-2-yl]propylcarbamate;
2,2,2-trifluoroethyl trans-3-[5-(6-methoxynaphthalen-1-yl)-1,3-dioxan-2-yl]propylcarbamate;
phenyl trans-3-[5-(6-methoxynaphthalen-1-yl)-1,3-dioxan-2-yl]propylcarbamate;
2-amino-2-oxoethyl trans-3-[5-(6-cyclopropylmethoxynaphthalen-1-yl)-1,3-dioxan-2-yl]propylcarbamate;
4-chlorophenyl trans-3-[5-(6-cyclopropylmethoxynaphthalen-1-yl)-1,3-dioxan-2-yl]propylcarbamate;
2,2,2-trifluoroethyl trans-3-[5-(6-cyclopropylmethoxynaphthalen-1-yl)-1,3-dioxan-2-yl]propylcarbamate;
2-amino-2-oxoethyl trans-3-[5-(6-phenylmethoxynaphthalen-1-yl)-1,3-dioxan-2-yl]propylcarbamate;
2-amino-2-oxoethyl trans-3-[5-(6-hydroxynaphthalen-1-yl)-1,3-dioxan-2-yl]propylcarbamate;
2-(methylamino)-2-oxoethyl trans-3-[5-(6-hydroxynaphthalen-1-yl)-1,3-dioxan-2-yl]propylcarbamate;
2-amino-2-oxoethyl trans-3-[5-(7-methoxynaphthalen-1-yl)-1,3-dioxan-2-yl]propylcarbamate;
2-(methylamino)-2-oxoethyl trans-3-[5-(7-methoxynaphthalen-1-yl)-1,3-dioxan-2-yl]propylcarbamate;
2,2,2-trifluoroethyl trans-3-[5-(7-methoxynaphthalen-1-yl)-1,3-dioxan-2-yl]propylcarbamate;
phenyl trans-3-[5-(7-methoxynaphthalen-1-yl)-1,3-dioxan-2-yl]propylcarbamate;
phenyl trans-3-[5-(naphthalen-2-yl)-1,3-dioxan-2-yl]propylcarbamate;
2-(methylamino)-2-oxoethyl trans-3-[5-(naphthalen-2-yl)-1,3-dioxan-2-yl]propylcarbamate; and
2,2,2-trifluoroethyl trans-3-[5-(naphthalen-2-yl)-1,3-dioxan-2-yl]propylcarbamate; or
said compound in the form of a base or an addition salt with an acid.

15. A method of using a compound of formula (I) as set forth in claim 1 as analgesic comprising administering to a patient in need thereof a therapeutically effective amount of a compound of formula (I) as set forth in claim 1, in the form of a pharmaceutically acceptable base or a salt, optionally, in combination with one more pharmaceutically acceptable excipients.

16. A method of using a compound of formula (I) as set forth in claim 1 as analgesic in the treatment of a disease in a patient comprising administering to said patient a therapeutically effective amount of a compound of formula (I) as set forth in claim 1, in the form of a pharmaceutically acceptable base or salt, optionally, in combination with one more pharmaceutically acceptable excipients, wherein said disease is selected from the group consisting of: acute or chronic pain, dizziness, vomiting, nausea, eating disorders, neurological and psychiatric pathological conditions, acute or chronic neurodegenerative diseases, epilepsy, sleep disorders, cardiovascular diseases, renal ischemia, cancers, disorders of the immune system, allergic diseases, parasitic, viral or bacterial infectious diseases, inflammatory diseases, osteoporosis, ocular conditions, pulmonary conditions, gastrointestinal diseases or urinary incontinence.

17. The method as set forth in claim 16, wherein compound of formula I in which $R_1$ represents a naphthalenyl group optionally substituted with one or more halogen atoms or hydroxyl, cyano, nitro, $(C_1–C_3)$alkyl, $(C_1–C_3)$alkoxy, trifluoromethyl, trifluoromethoxy, benzyloxy, $(C_3–C_6)$cycloalkyl-O— or $(C_3–C_6)$-cycloalkyl$(C_1–C_3)$alkoxy groups, and said compound in the form of a base or an addition salt with an acid.

18. The method as set forth in claim 16, wherein compound of formula I in which $R_2$ represents either a group of general formula $CHR_3CONHR_4$, or a 2,2,2-trifluoroethyl group, or a phenyl group optionally substituted with one or more halogen atoms or cyano, nitro, $(C_1–C_3)$alkyl, $(C_1–C_3)$alkoxy, trifluoromethyl or trifluoromethoxy groups; and
wherein
$R_3$ represents a hydrogen atom;
$R_4$ represents a hydrogen atom or a $(C_1–C_3)$alkyl or (pyridin-4-yl)methyl group; and
said compound in the form of a base or an addition salt with an acid.

19. The method as set forth in claim 16, wherein compound of formula I in which n represents 2 or 3; and said compound is in the form of a base, an addition salt with an acid.

20. The method as set forth in claim 16, wherein compound of formula I is selected from the group consisting of:
2-amino-2-oxoethyl trans-3-[5-(naphthalen-1-yl)-1,3-dioxan-2-yl]propylcarbamate;
2-(methylamino)-2-oxoethyl trans-2-[5-(naphthalen-1-yl)-1,3-dioxan-2-yl]ethylcarbamate;
2-(methylamino)-2-oxoethyl trans-3-[5-(naphthalen-1-yl)-1,3-dioxan-2-yl]propylcarbamate;
2,2,2-trifluoroethyl trans-2-[5-(naphthalen-1-yl)-1,3-dioxan-2-yl]ethylcarbamate;
2,2,2-trifluoroethyl trans-3-[5-(naphthalen-1-yl)-1,3-dioxan-2-yl]propylcarbamate;
phenyl trans-2-[5-(naphthalen-1-yl)-1,3-dioxan-2-yl]ethylcarbamate;
phenyl trans-3-[5-(naphthalen-1-yl)-1,3-dioxan-2-yl]propylcarbamate;
2-amino-2-oxoethyl trans-3-[5-(4-chloronaphthalen-1-yl)-1,3-dioxan-2-yl]propylcarbamate;
2-(methylamino)-2-oxoethyl trans-3-[5-(4-chloronaphthalen-1-yl)-1,3-dioxan-2-yl]propylcarbamate;
2-(methylamino)-2-oxoethyl trans-3-[5-(6-chloronaphthalen-1-yl)-1,3-dioxan-2-yl]propylcarbamate;
2-amino-2-oxoethyl trans-3-[5-(6-methoxynaphthalen-1-yl)-1,3-dioxan-2–7yl]propylcarbamate;
2-amino-2-oxoethyl cis-3-[5-(6-methoxynaphthalen-1-yl)-1,3-dioxan-2-yl]propylcarbamate;
2-(methylamino)-2-oxoethyl trans-2-[5-(6-methoxynaphthalen-1-yl)-1,3-dioxan-2-yl]ethylcarbamate;
4-chlorophenyl trans-2-[5-(6-methoxynaphthalen-1-yl)-1,3-dioxan-2-yl]ethylcarbamate;
2,2,2-trifluoroethyl trans-2-[5-(6-methoxynaphthalen-1-yl)-1,3-dioxan-2-yl]ethylcarbamate;
2-(methylamino)-2-oxoethyl trans-3-[5-(6-methoxynaphthalen-1-yl)-1,3-dioxan-2-yl]propylcarbamate;

2-(ethylamino)-2-oxoethyl trans-3-[5-(6-methoxynaphthalen-1-yl)-1,3-dioxan-2-yl]propylcarbamate;

2-[(pyridin-4-yl)methylamino]-2-oxoethyl trans-3-[5-(6-methoxynaphthalen-1-yl)-1,3-dioxan-2-yl]propylcarbamate;

2,2,2-trifluoroethyl trans-3-[5-(6-methoxynaphthalen-1-yl)-1,3-dioxan-2-yl]propylcarbamate;

phenyl trans-3-[5-(6-methoxynaphthalen-1-yl)-1,3-dioxan-2-yl]propylcarbamate;

2-amino-2-oxoethyl trans-3-[5-(6-cyclopropylmethoxynaphthalen-1-yl)-1,3-dioxan-2-yl]propylcarbamate;

4-chlorophenyl trans-3-[5-(6-cyclopropylmethoxynaphthalen-1-yl)-1,3-dioxan-2-yl]propylcarbamate;

2,2,2-trifluoroethyl trans-3-[5-(6-cyclopropylmethoxynaphthalen-1-yl)-1,3-dioxan-2-yl]propylcarbamate;

2-amino-2-oxoethyl trans-3-[5-(6-phenylmethoxynaphthalen-1-yl)-1,3-dioxan-2-yl]propylcarbamate;

2-amino-2-oxoethyl trans-3-[5-(6-hydroxynaphthalen-1-yl)-1,3-dioxan-2-yl]propylcarbamate;

2-(methylamino)-2-oxoethyl trans-3-[5-(6-hydroxynaphthalen-1-yl)-1,3-dioxan-2-yl]propylcarbamate;

2-amino-2-oxoethyl trans-3-[5-(7-methoxynaphthalen-1-yl)-1,3-dioxan-2-yl]propylcarbamate;

2-(methylamino)-2-oxoethyl trans-3-[5-(7-methoxynaphthalen-1-yl)-1,3-dioxan-2-yl]propylcarbamate;

2,2,2-trifluoroethyl trans-3-[5-(7-methoxynaphthalen-1-yl)-1,3-dioxan-2-yl]propylcarbamate;

phenyl trans-3-[5-(7-methoxynaphthalen-1-yl)-1,3-dioxan-2-yl]propylcarbamate;

phenyl trans-3-[5-(naphthalen-2-yl)-1,3-dioxan-2-yl]propylcarbamate;

2-(methylamino)-2-oxoethyl trans-3-[5-(naphthalen-2-yl)-1,3-dioxan-2-yl]propylcarbamate; and 2,2,2-trifluoroethyl trans-3-[5-(naphthalen-2-yl)-1,3-dioxan-2-yl]propylcarbamate; or said compound in the form of a base or an addition salt with an acid.

21. The compound of formula (I) as set forth in claim 1, which is chosen from:

2-(methylamino)-2-oxoethyl trans-3-[5-(6-methoxynaphthalen-1-yl)-1,3-dioxan-2-yl]propylcarbamate;

2-(ethylamino)-2-oxoethyl trans-3-[5-(6-methoxynaphthalen-1-yl)-1,3-dioxan-2-yl]propylcarbamate;

2-(methylamino)-2-oxoethyl trans-2-[5-(naphthalen-1-yl)-1,3-dioxan-2-yl]ethylcarbamate;

2-(methylamino)-2-oxoethyl trans-3-[5-(naphthalen-1-yl)-1,3-dioxan-2-yl]propylcarbamate;

2-(methylamino)-2-oxoethyl trans-3-[5-(4-chloronaphthalen-1-yl)-1,3-dioxan-2-yl]propylcarbamate;

2-(methylamino)-2-oxoethyl trans-3-[5-(6-chloronaphthalen-1-yl)-1,3-dioxan-2-yl]propylcarbamate; and 2-amino-2-oxoethyl trans-3-[5-(6-methoxynaphthalen-1-yl)-1,3-dioxan-2-yl]propylcarbamate; or said compound in the form of a base or an addition salt with an acid.

22. The composition as set forth in claim 10, wherein compound of formula I is selected from the group consisting of:

2-(methylamino)-2-oxoethyl trans-3-[5-(6-methoxynaphthalen-1-yl)-1,3-dioxan-2-yl]propylcarbamate;

2-(ethylamino)-2-oxoethyl trans-3-[5-(6-methoxynaphthalen-1-yl)-1,3-dioxan-2-yl]propylcarbamate;

2-(methylamino)-2-oxoethyl trans-2-[5-(naphthalen-1-yl)-1,3-dioxan-2-yl]ethylcarbamate;

2-(methylamino)-2-oxoethyl trans-3-[5-(naphthalen-1-yl)-1,3-dioxan-2-yl]propylcarbamate;

2-(methylamino)-2-oxoethyl trans-3-[5-(4-chloronaphthalen-1-yl)-1,3-dioxan-2-yl]propylcarbamate;

2-(methylamino)-2-oxoethyl trans-3-[5-(6-chloronaphthalen-1-yl)-1,3-dioxan-2-yl]propylcarbamate; and 2-amino-2-oxoethyl trans-3-[5-(6-methoxynaphthalen-1-yl)-1,3-dioxan-2-yl]propylcarbamate; or said compound in the form of a base or an addition salt with an acid.

23. The method as set forth in claim 16, wherein compound of formula I is selected from the group consisting of:

2-(methylamino)-2-oxoethyl trans-3-[5-(6-methoxynaphthalen-1-yl)-1,3-dioxan-2-yl]propylcarbamate;

2-(ethylamino)-2-oxoethyl trans-3-[5-(6-methoxynaphthalen-1-yl)-1,3-dioxan-2-yl]propylcarbamate;

2-(methylamino)-2-oxoethyl trans-2-[5-(naphthalen-1-yl)-1,3-dioxan-2-yl]ethylcarbamate;

2-(methylamino)-2-oxoethyl trans-3-[5-(naphthalen-1-yl)-1,3-dioxan-2-yl]propylcarbamate;

2-(methylamino)-2-oxoethyl trans-3-[5-(4-chloronaphthalen-1-yl)-1,3-dioxan-2-yl]propylcarbamate;

2-(methylamino)-2-oxoethyl trans-3-[5-(6-chloronaphthalen-1-yl)-1,3-dioxan-2-yl]propylcarbamate; and 2-amino-2-oxoethyl trans-3-[5-(6-methoxynaphthalen-1-yl)-1,3-dioxan-2-yl]propylcarbamate; or said compound in the form of a base or an addition salt with an acid.

\* \* \* \* \*